US008641745B2

(12) United States Patent
Warner et al.

(10) Patent No.: US 8,641,745 B2
(45) Date of Patent: Feb. 4, 2014

(54) DEVICE AND METHOD FOR EXTRACTING HEAT FROM THE PALM OF A HAND

(75) Inventors: Brett W. Warner, Austin, TX (US);
Anna Ercius Warner, Austin, TX (US)

(73) Assignee: Cool Palms LLC, Austin, TX (US)

( * ) Notice: Subject to any disclaimer, the term of this patent is extended or adjusted under 35 U.S.C. 154(b) by 0 days.

(21) Appl. No.: 12/843,433

(22) Filed: Jul. 26, 2010

(65) Prior Publication Data

US 2011/0022138 A1 Jan. 27, 2011

Related U.S. Application Data (60) Provisional application No. 61/228,299, filed on Jul. 24, 2009.

(51) Int. Cl.
*A61F 7/02* (2006.01)
*A61F 7/10* (2006.01)

(52) U.S. Cl.
USPC .......................................................... 607/111

(58) Field of Classification Search
USPC .......................................................... 607/111
See application file for complete search history.

(56) References Cited

U.S. PATENT DOCUMENTS

| 4,527,566 A * | 7/1985 | Abare ............................ 607/112 |
| 4,625,729 A * | 12/1986 | Roney ............................ 607/108 |
| 4,628,918 A * | 12/1986 | Johnson, Jr. ..................... 602/13 |
| 4,628,932 A * | 12/1986 | Tampa ........................... 607/108 |
| 5,050,596 A * | 9/1991 | Walasek et al. ................ 607/111 |
| 5,165,402 A * | 11/1992 | McCoy .......................... 607/108 |
| 5,514,170 A * | 5/1996 | Mauch ........................... 607/109 |
| 5,766,235 A * | 6/1998 | Kostopoulos .................. 607/114 |
| 5,956,772 A * | 9/1999 | Widdemer ........................ 2/167 |
| 5,991,926 A * | 11/1999 | Lakusiewicz ..................... 2/168 |
| 6,141,801 A * | 11/2000 | Helenick ........................... 2/159 |
| 6,149,617 A * | 11/2000 | McNally et al. ................ 602/62 |
| D456,521 S * | 4/2002 | Griffin et al. ................. D24/206 |
| 6,772,445 B2 * | 8/2004 | Yeager ............................. 2/170 |
| 6,895,598 B1 * | 5/2005 | Sokolowski ...................... 2/159 |
| 6,931,875 B1 * | 8/2005 | Allen et al. ..................... 62/237 |
| 6,936,018 B2 * | 8/2005 | Chalek ............................. 602/2 |
| 6,944,884 B1 * | 9/2005 | Sokolowski .................... 2/161.1 |
| 2002/0026226 A1 * | 2/2002 | Ein ............................... 607/108 |
| 2003/0109910 A1 * | 6/2003 | Lachenbruch et al. ........ 607/108 |
| 2003/0221241 A1 * | 12/2003 | Rivera et al. ...................... 2/170 |
| 2004/0147990 A1 * | 7/2004 | Graham et al. ................ 607/111 |
| 2004/0244090 A1 * | 12/2004 | Langer ............................. 2/160 |
| 2005/0070980 A1 * | 3/2005 | Noonan ......................... 607/108 |
| 2005/0262871 A1 * | 12/2005 | Bailey-Weston ............ 62/457.2 |
| 2006/0036304 A1 * | 2/2006 | Cordani et al. ............... 607/108 |

(Continued)

OTHER PUBLICATIONS

Grahn et al. Heat extraction through the palm of one hand improves aerobic exercise endurance in a hot environment, J. Appl. Physiol., May 5, 2005, pp. 972-978, vol. 99.

(Continued)

*Primary Examiner* — Linda Dvorak
*Assistant Examiner* — Kaitlyn Smith
(74) *Attorney, Agent, or Firm* — The Webb Law Firm (57) ABSTRACT

A device for extracting thermal energy from the core body of an individual via the palm thereof during or after physical exertion activity by that individual, wherein the device includes (a) an enclosure containing a cold-maintaining substance, wherein the enclosure is not larger than the palm; and (b) securing means attached to the enclosure for securing the enclosure against the palm.

2 Claims, 7 Drawing Sheets

(56) References Cited

U.S. PATENT DOCUMENTS

| | | | |
|---|---|---|---|
| 2006/0293736 A1* | 12/2006 | Mariano et al. | 607/111 |
| 2007/0112400 A1* | 5/2007 | Hamilton et al. | 607/104 |
| 2007/0185555 A1* | 8/2007 | Partrich et al. | 607/114 |
| 2008/0064996 A1* | 3/2008 | Bretl et al. | 602/21 |
| 2009/0076574 A1* | 3/2009 | Noel | 607/109 |
| 2009/0112134 A1* | 4/2009 | Avni | 601/15 |
| 2009/0287280 A1* | 11/2009 | Wong et al. | 607/96 |
| 2009/0326622 A1* | 12/2009 | Johnson et al. | 607/111 |
| 2010/0087900 A1* | 4/2010 | Flint | 607/104 |
| 2010/0274333 A1* | 10/2010 | Dunshee et al. | 607/114 |
| 2011/0029051 A1* | 2/2011 | Ross | 607/108 |
| 2011/0099676 A1* | 5/2011 | Getzwiller | 2/16 |
| 2011/0106227 A1* | 5/2011 | Desiderio et al. | 607/111 |

OTHER PUBLICATIONS

Goosey-Tolfrey et al. The effectiveness of hand cooling at reducing exercise-induced hyperthermia and improving distance-race performance in wheelchair and able-bodied athletes, J. Appl. Physiol., Apr. 24, 2008, pp. 37-43, vol. 105.

* cited by examiner

DEVICE AND METHOD FOR EXTRACTING HEAT FROM THE PALM OF A HAND

CROSS REFERENCE TO RELATED APPLICATIONS

This application claims the benefit of U.S. Provisional Patent Application No. 61/228,299 filed Jul. 24, 2009, and entitled "Device and Method for Extracting Heat from the Palm of a Hand," the contents of which are incorporated herein by reference.

BACKGROUND OF THE INVENTION

1. Field of the Invention

The present invention relates to an athletic training and conditioning device and, more particularly, to a device and method for accelerating heat extraction via an individual's palm during and after physical exercise by that individual.

2. Description of Related Art

Heat is scientifically proven to be a limiting factor in exercise. When the body's core is kept cool, an individual is able to perform better, longer, and more confidently. The palm of the hand is scientifically shown to be a natural radiator point on the body. Special blood vessels, found under the palm surface called arteriovenous anastomoses, bring heated blood from the body's core and dissipate heat at the body's extremities.

As is known in the art, enhanced heat extraction from a person's body should improve performance capacity of the person. Specifically, according to the article entitled "Heat Extraction Through the Palm of One Hand Improves Aerobic Exercise Endurance In a Hot Environment", authored by Dennis Grahn, Vinh Cao, and Craig Heller of the Department of Biological Sciences, Stanford University, Stanford Calif., published on May 5, 2005 in the Journal of Applied Physiology (hereinafter "the Heat Extraction article"), incorporated herein in its entirety by reference, it is asserted that "[i]n situations where the accumulation of internal heat limits physical performance, enhanced heat extraction from the body should improve performance capacity. The combined application of local subatmospheric pressure (35-45 mmHg) to an entire hand (to increase blood volume) and a heat sink (18-22° C.) to the palmar surface were used to draw heat out of the circulating blood."

The Heat Extraction article discloses a heat extraction device of AVAcore Technologies, Ann Arbor, Mich., commercially marketed as the CoreControl that includes "a rigid chamber into which a hand could be inserted through an elastic structure that formed a flexible airtight seal around the wrist. The rigid chamber [is] connected to a pressure sensor, a pressure relief valve (cracking pressure −45 mmHg), and a vacuum source [the building in-house system or a commercially available vacuum pump (⅒th horsepower; model SR-0015-VP, Thomas Industries, Louisville, Ky.)]. A water trap consisting of a 1,000-ml filter flask (VWR) [is] plumbed into the vacuum line upstream of the vacuum pump. Activation of the vacuum pump [creates] a slight subatmospheric chamber pressure (−40 mmHg). Inside the chamber, the palm [rests] on a curved metal surface that [is] maintained at 22° C. or 18° C. (−0.5° C.) by perfusion of the temperature-controlled water beneath it. The hand interface [is] tethered via Tygon tubing (8-mm bore, 3-mm wall) to a temperature-controlled heated/refrigerated circulating water bath (model RM 6, Lauda, Konigshofen, Germany) that [regulates] the temperature of the circulating water. The hand interface device [is] suspended from the ceiling by an elastic cord so that the subject [can] maintain normal arm movements while walking."

The Heat Extraction article discusses the naturally occurring phenomenon of the radiator-like properties of the palms of the hands and the soles of the feet in the context of how "[t]he heat extraction technology takes advantage of adaptations for heat transfer that are features of certain nonhairy skin surfaces. The arteriovenous anastomoses (AVAs) and venous plexuses in the palms of the hands and the soles of the feet are effective mechanisms for heat dissipation when core body temperature rises. [The heat extraction] device previously described is used to apply a 35 to 45-mmHg subatmospheric pressure to an entire hand to draw blood into the hand and increase the filling of the venous plexus underlying the palmar surface. A heat sink applied to that palm extracts heat and cools the venous blood. In the present study, [the researchers] used the device in an attempt to slow the rate of core temperature rise of individuals engaged in aerobic exercise in a hot environment. The hypothesis to be tested in these studies was that manipulation of heat balance by enhancing heat loss from the hand can increase the endurance capacity of individuals exercising at a fixed workload in a hot environment."

Of note, in another article entitled "The Effectiveness of Hand Cooling at Reducing Exercise-Induced Hyperthermia and Improving Distance-Race Performance in Wheelchair and Able-Bodied Athletes", authored by Victoria Goosey-Tolfrey, Michelle Swainson, Craig Boyd, Greg Atkinson, and Keith Tolfrey, published on Apr. 24, 2008 in the Journal of Applied Physiology, incorporated herein in its entirety by reference, also discusses the general concept of hand cooling to increase performance in postexercise hyperthermic subjects.

The aforementioned prior art CoreControl device, which is disclosed in U.S. Pat. No. 6,656,208 to Grahn et al., incorporated herein in its entirety by reference, is limited in its applications and has various other disadvantages associated therewith. First, such a device is expensive in that its current day cost is $3,000.00 per unit. Second, such a device is not portable in that it is weighty and cumbersome and needs to be set-up prior to exercise and monitored while in use in a fixed location, as evidenced in FIG. 1 of the Grahn patent. Third, the device is over-engineered in that it requires motors and vacuums that are used to increase blood flow, even though it is accepted that blood flow increases naturally during exercise. Fourth, the moving parts and complex operation make it impractical for use by an average person. This is evidenced by the fact that the CoreControl is marketed toward sports organizations and other entities having personnel dedicated to working with the individual who would use the device.

It is, therefore, desirable to overcome the above problems and others by providing a device for extracting heat from the palm of a hand, wherein such a device is inexpensive, easy to manufacture, portable, comfortable to use, easy to operate, and overall practical in its implementation.

SUMMARY OF THE INVENTION

Accordingly, the present invention includes a device and method for accelerating heat extraction via an individual's palm during and after physical exercise by that individual.

The present invention is directed to maintaining a cool surface to the palm of the hand, thereby cooling the blood in the palm more effectively and efficiently than the outside air. The cooled blood from the palm is brought back to the body's core and helps maintain peak performance periods for heart rate, temperature and muscle output. Individuals wearing the embodiment of the invention set forth below are found to be more confident, more comfortable, and feel more alert during exercise. The present invention takes advantage of, and increases the efficiency of, the body's natural cooling process.

In one embodiment, a device for extracting thermal energy from the core body of an individual via the palm thereof during or after physical exertion activity by that individual includes (a) an enclosure containing a cold-maintaining substance, wherein the enclosure is not larger than the palm; and (b) securing means attached to the enclosure for securing the enclosure against the palm. The securing means include a first strap extending from a first end of the enclosure, wherein the first strap includes on one side thereof a hook and loop fastener arrangement; and (b) a buckle fluidly secured to a second end opposite the first end of the enclosure, wherein the buckle is sized to receive the first strap therethrough. The second end of the enclosure may include a second strap extending therefrom, wherein a free end of the second strap is connected to the buckle. The cold-maintaining substance may include a gel containing water and a sodium salt of cross-linked polyacrylic acid. The device may include a pack containing the cold-maintaining substance, wherein the pack is contained within the enclosure. The device may include an opening and closing mechanism defined within the enclosure, wherein the pack is removable from the enclosure when the opening and closing mechanism is in an open state. The opening and closing mechanism may be a zipper, an interlocking tongue and groove arrangement, another hook and loop fastener arrangement, a clasp, a button, or overlapping flaps. The enclosure may be 2 inches by 3.5 inches and the first strap may be 1 inch by 5.5 inches. The enclosure may be 2.5 inches by 4 inches and the first strap may be 1 inch by 8 inches. The enclosure may be constructed of nylon polyethylene laminate. The first strap may be stitched to the enclosure and the hook and loop fastener arrangement may be stitched to the first strap. The enclosure with the cold-maintaining substance contained therein conforms to the contours of the palm when the palm is open and closed. The enclosure includes a first side and a second side, wherein the first side may include a wicking material and wherein the second side may include an insulating material.

In one embodiment, a method for extracting thermal energy from the core body of an individual via the palm thereof during or after a physical exertion activity by that individual includes the steps of (a) placing a device in a refrigerated location, wherein the device includes: (i) an enclosure containing a cold-maintaining substance, wherein the enclosure is not larger than the palm; (ii) securing means attached to the enclosure for securing the enclosure against the palm; (b) removing the device from the refrigerated location prior to the physical exertion activity; (c) securing the device against the palm; and (d) engaging in the physical exertion activity. The securing means include (a) a first strap extending from a first end of the enclosure, wherein the first strap includes on one side thereof a hook and loop fastener arrangement; and (b) a buckle fluidly secured to a second end opposite the first end of the enclosure, wherein the buckle is sized to receive the first strap therethrough. The step of securing the device against the palm includes the steps of: (a) holding the enclosure against the palm; (b) looping a free end of the first strap around the back of the hand in a first direction; (c) inserting the free end of the first strap through the buckle and looping the free end across the back of the hand in a second direction opposite the first direction; (d) securing a plurality of hooks of the hook and loop fastener arrangement to a plurality of loops of the hook and loop fastener arrangement. The cold-maintaining substance may include a gel containing water and a sodium salt of cross-linked polyacrylic acid. The device may include a pack containing the cold-maintaining substance, wherein the pack is contained within the enclosure. The device may include an opening and closing mechanism defined within the enclosure, wherein the pack is removable from the enclosure when the opening and closing mechanism is in an open state. The aforementioned method may also include the steps of (a) opening the opening and closing mechanism; (b) removing the pack from the enclosure; (c) inserting a new pack into the enclosure, wherein the new pack is colder than the removed pack; and (d) closing the opening and closing mechanism.

The biophysical principles discussed in the aforementioned articles are incorporated herein and are to be utilized, in addition to the knowledge of those having ordinary skill in the art, to appreciate the underlying hand cooling principles and benefits of hand cooling, as they apply to improving performance.

Still other desirable features of the invention will become apparent to those of ordinary skill in the art upon reading and understanding the following detailed description, taken with the accompanying drawings, wherein like reference numerals represent like elements throughout.

DETAILED DESCRIPTION OF THE INVENTION

The present invention will now be described with reference to the accompanying figures. It is to be understood that the specific device illustrated in the attached figures and described in the following specification is simply an exemplary embodiment of the present invention. Hence, specific dimensions and other physical characteristics related to the embodiments disclosed herein are not to be considered as limiting.

Figure 1:
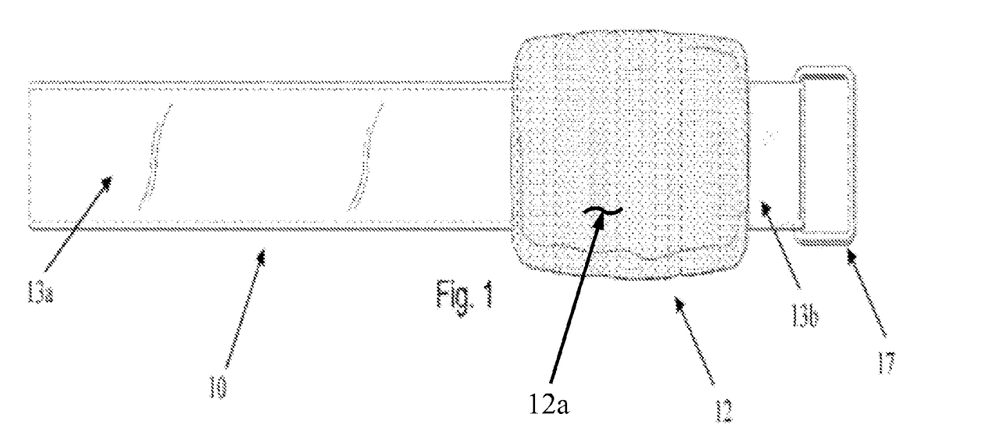
FIG. 1 is a top plan view of a heat extracting device in an open position, in accordance with the present invention.
Figure 2:
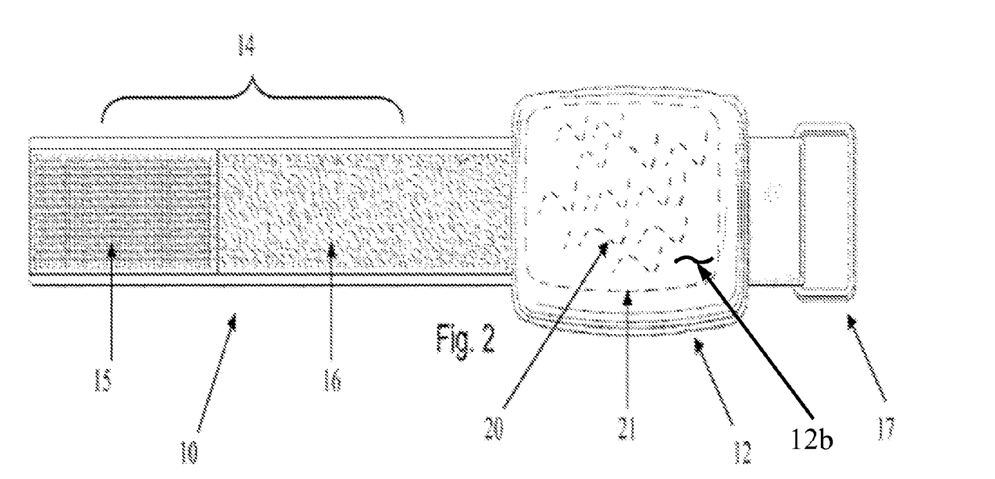
FIG. 2 is a bottom plan view of the heat extracting device of FIG. 1.
Figure 3:
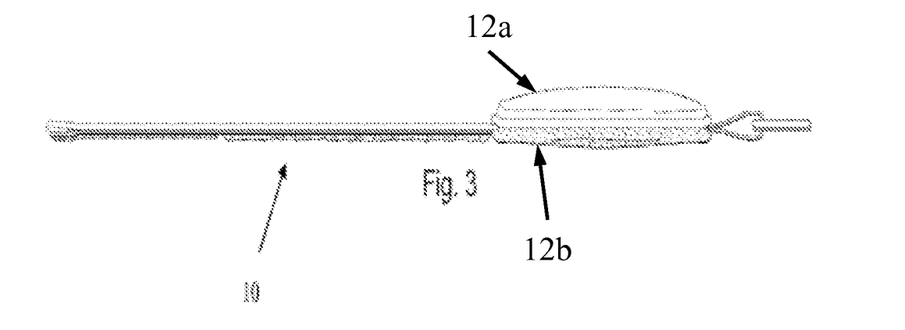
FIG. 3 is a side elevation view of the heat extracting device of FIG. 1.
Figure 5:
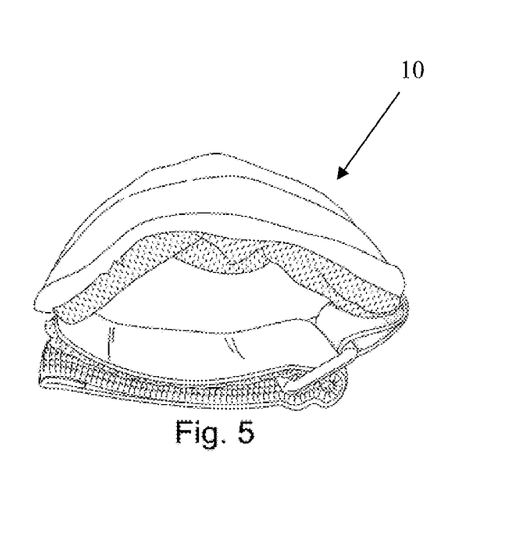
FIG. 5 is a perspective view of the heat extracting device of FIG. 1 in a secured position.
Figure 6:
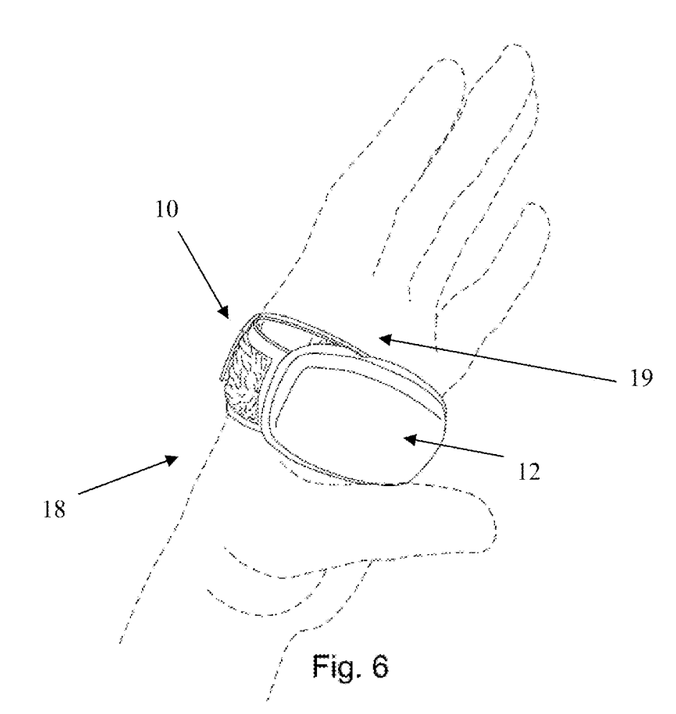
FIG. 6 is a perspective view of the heat extracting device of FIG. 1 secured to a palm of a hand, in accordance with the present invention.
Figure 7:
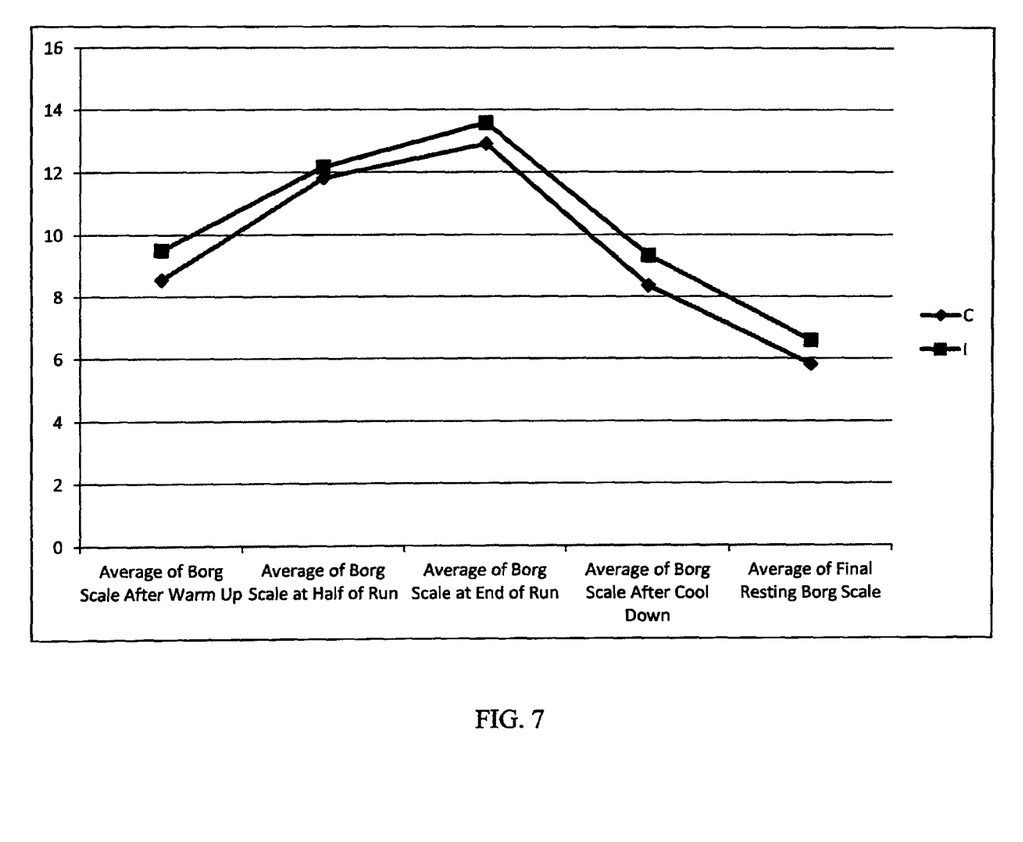
FIG. 7 is a graph of Borg scale results.
Figure 8:
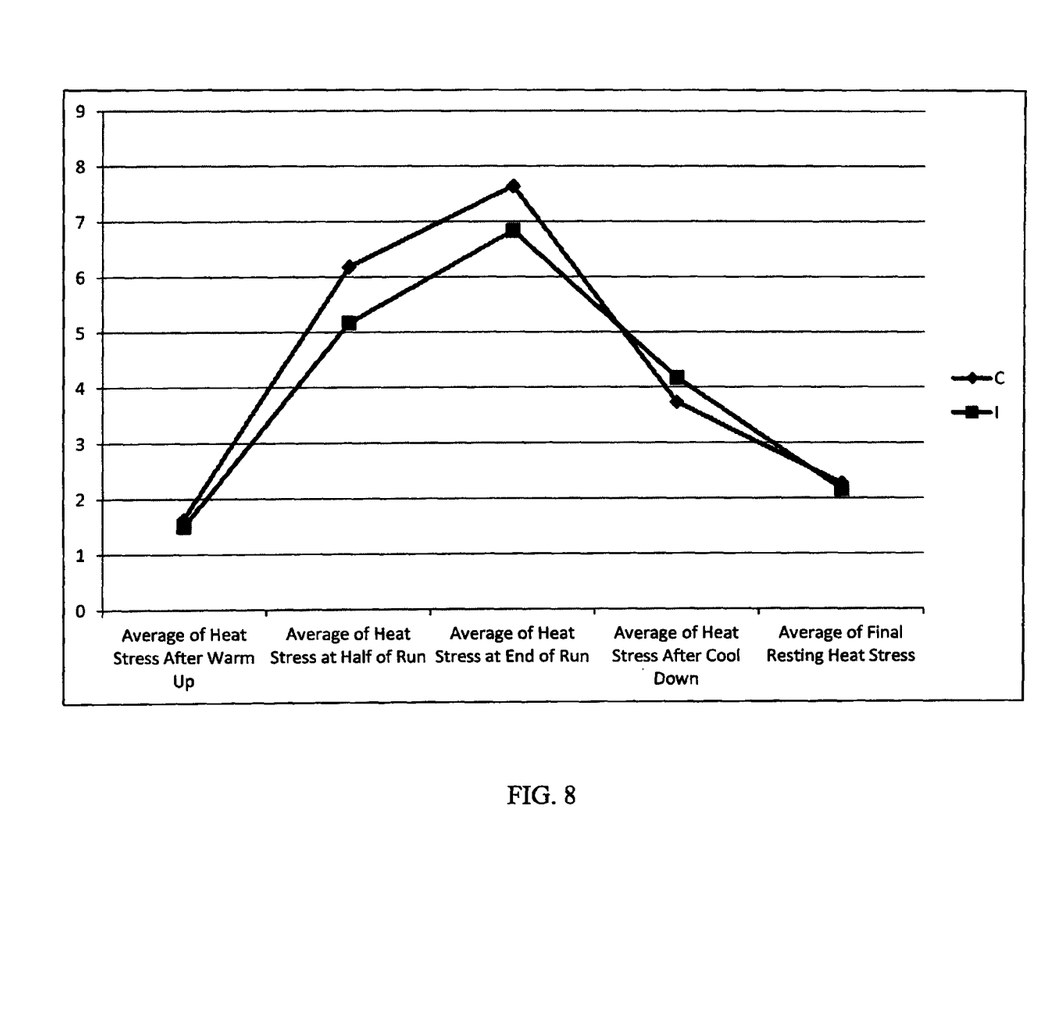
FIG. 8 is a graph of heat stress results.
Figure 9:
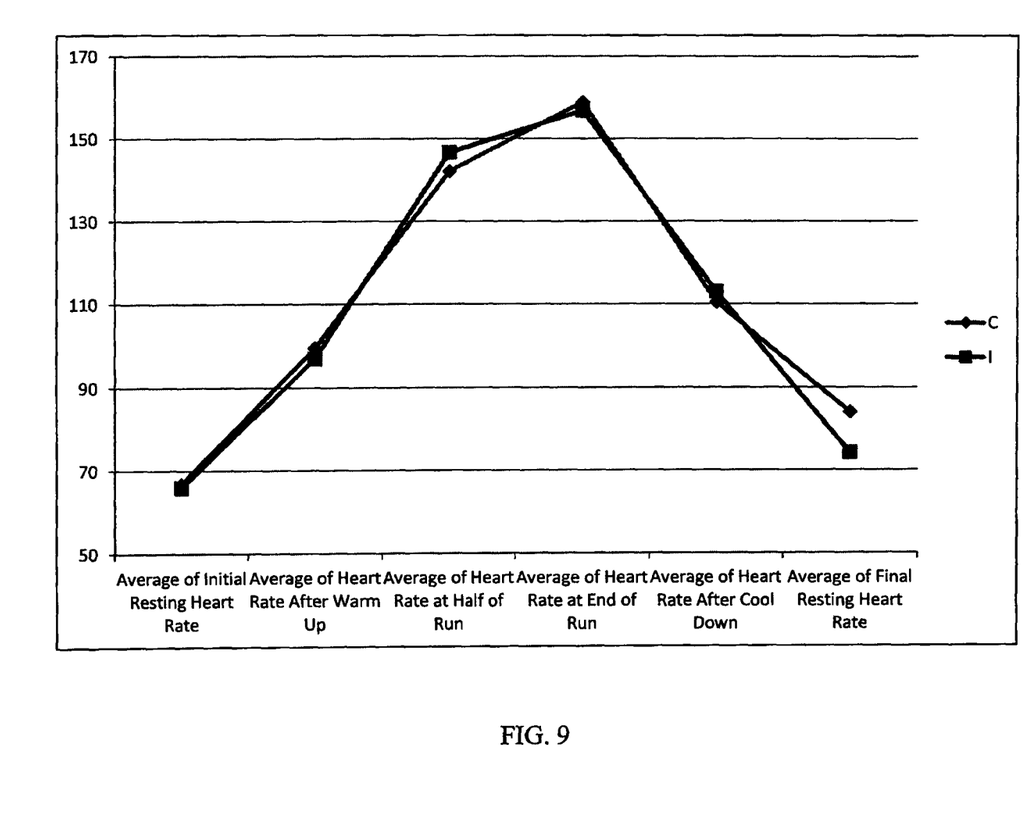
FIG. 9 is a graph of heart rate results.
Figure 10:
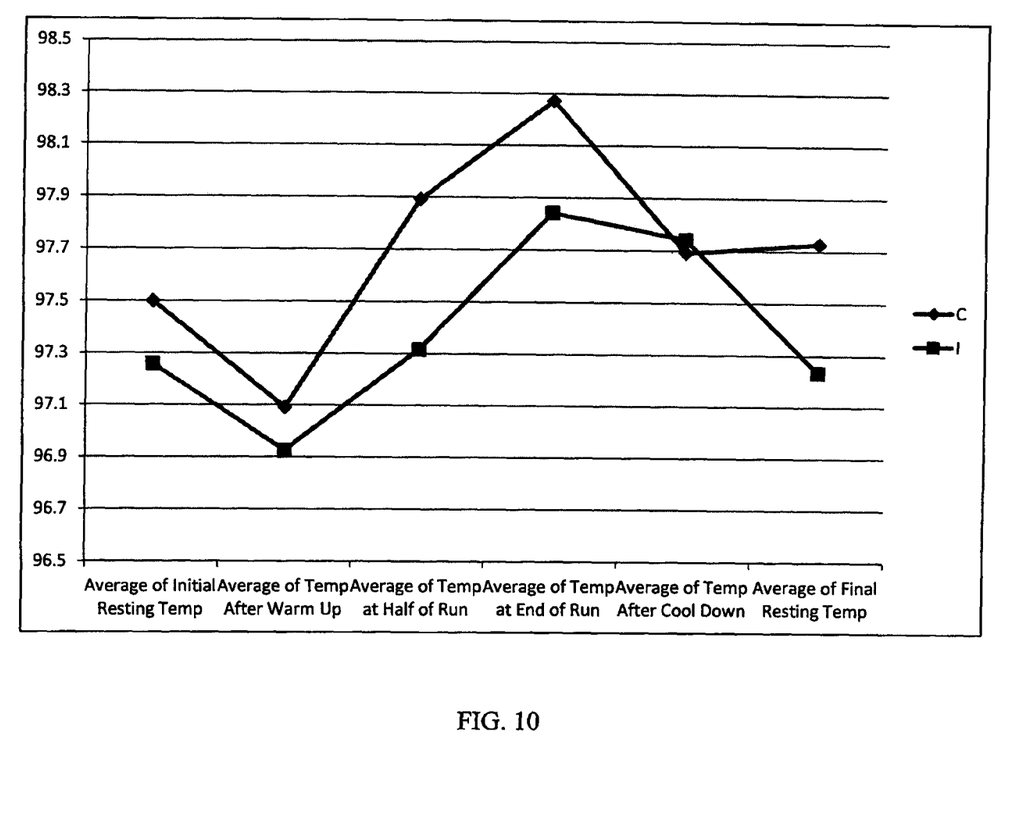
FIG. 10 is a graph of temperature results.

FIGS. 1-3 depict a heat extracting device 10 for accelerating heat extraction via an individual's palm during and after physical exercise by that individual. The heat extracting device 10 includes an enclosure 12 having at least one or more straps 13a, 13b attached at opposite ends thereof. One of the straps 13a may be longer than the other strap 13b in order to accommodate a hook and loop fastener arrangement 14 thereon. The hook and loop fastener arrangement 14 includes corresponding hooks 15 and loops 16 and may be of the Velcro® brand, however, it is to be understood that any suitable hook and loop fastener arrangement may be utilized. The end of the strap 13b not attached to the enclosure 12 may include a buckle 17 for allowing the strap 13b to be looped therethrough and folded over such that at least a portion of the hooks 15 align with and engage a corresponding portion of the loops 16. The resultant secured configuration of the heat extracting device 10 is depicted in FIG. 5. This secured configuration allows the heat extracting device 10 to be secured around a hand 18 of an individual, with the enclosure 12 being situated adjacent to a palm 19 of the hand 18, as shown in FIG. 6.

It is to be understood that the aforementioned enclosure 12, straps 13a, 13b, hook and loop fastener arrangement 14, and buckle 17 may assume different physical dimensions to accommodate the intended purpose. For example, the enclosure 12 and the straps 13a, 13b may be of varying sizes to accommodate differently-sized hands, such as those of males and females. In one embodiment, the enclosure 12 measures 2.5"×4" and the strap 13a measures 1" by 8". This embodiment corresponds to the palm of an average adult male. In another embodiment, the enclosure 12 measures 2"×3.5" and the strap 13a measures 1" by 5.5". This embodiment corresponds to the palm of an average adult female. However, it is to be understood that there exist other suitable dimensions not expressly disclosed herein. When reference is made herein that the enclosure 12 is not larger than the palm, this is to be taken in the context of the size of a palm of an average adult.

Other buckle designs may include, but are not limited to, slotted designs having two or more slots, or buckle designs found on backpacks, for example. Generally, the enclosure 12 is dimensioned to comfortably fit in the palm 19 of the hand 18 so that it may be held during exercises, such as running, for example.

It is to be understood that some of the aforementioned components may be modified in or may be absent from different configurations of the present invention. For example, the buckle 17 may be directly attached to the enclosure 12 (without the need for the intermediary connection via the strap 13b) or an opening sized to receive the strap 13a may be defined along an edge of the enclosure 12. Another hook and loop fastener arrangement may include the use of the existing hooks 15, but having the loops be situated along the length of the enclosure 12. Other contemplated, but not limiting embodiments, may forego the use of the hook and loop fastener arrangement 14, and may utilize an elastic strap with opposite ends thereof attached to respective opposite ends of the enclosure 12. Other securing mechanisms may include, but are not limited to, straps with clips, clasps/buttons with corresponding holes, and buckling arrangements. In yet a further embodiment, the enclosure 12 may be attached onto a strap, as opposed to having one or more straps extend from ends of the enclosure 12. It is to be understood that the various components discussed herein may be secured or attached to each other using various known methods in the art including, but not limited to, stitching and gluing. In yet another embodiment, the enclosure 12 may be embodied in glove-form, thereby foregoing the use of a strap or additional securing mechanism altogether.

In one embodiment, the enclosure 12 is constructed of a nylon polyethylene laminate, however it is to be understood that any suitable material, such as vinyl, may alternatively be employed. The material 12a of the enclosure 12 that is intended to be placed against the palm 19 may be a mesh fabric or any other suitable fabric having wicking properties that allows for maximum heat transfer between the skin of the palm 19 and the heat extracting device 10. The material 12b of the enclosure 12 that is not adjacent to the palm 19 may be insulated nylon or any suitable material that reduces loss of cooling from within the enclosure 12. The enclosure 12 may be constructed to withstand contact with harsh elements of the environment, including sweat or sharp objects. Thus, the enclosure 12 may also be constructed of material, such as high strength puncture-resistant plastic or non-oxidizing synthetic material, that is resistant to these harsh elements. The material may also be heat-conductive to expedite heat extraction. Because the enclosure 12 is used adjacent the skin and may be subject to friction thereagainst, the enclosure 12 may include soft surfaces, such as brushed polyester/nylon, or other suitable surface material. Additionally, it is contemplated that the enclosure 12 or any other component of the heat extracting device 10 may include bactericidal agents to prevent the growth of mildew or other bacteria.

The enclosure 12 includes a cold-maintaining substance 20 contained therein. The cold-maintaining substance 20 may be a gel containing water and sodium salt of cross-linked polyacrylic acid, known as superabsorbent polymers (SAPs). As is known in the art, SAPS, or absorbent polymers, absorbent gels, super soakers, super slurpers, and gel crystals, are materials that swell in water to form a clear gel made up of separate, individual particles. Unlike a sponge, in which water can be easily wrung out, the hydrated gel particles retain the absorbed water even under pressure. This unique ability to hold absorbed water, even against pressure, is the primary benefit of utilizing superabsorbent polymers in the present invention. The most common form of superabsorbents is a dry, white/off-white powder that looks like table salt or sugar. However, some dry SAP granules are as large as rock salt, or as small as talcum powder. As is known in the art, absorbent polymers can vary in their absorption capacity, and even in their speed of absorption; some are fast and some are slow. In deionized water, most superabsorbents will absorb at least 200 times their weight. The cold-maintaining substance 20 is designed to be flexible when frozen, not unlike the gel material used in connection with prior art cold-therapy gel packs, such as the GelPax brand gel pack distributed by Source One International, Inc. of North Vancouver, B.C., Canada. It is to be understood that any suitable cold-maintaining substance 20 should maintain a cold or cool temperature for an extended duration. The cold-maintaining substance 20 may maintain a flexible state regardless of the temperature thereof. Thus, the enclosure 12 with the cold-maintaining substance 20 contained therein, is able to conform to the contours of the palm 19 and is designed to maximize surface contact with the palm 19 in both an open and closed hand. In any case, it is to be understood that any suitable cold-maintaining substance 20 may be utilized in connection with the present invention.

Figure 4:
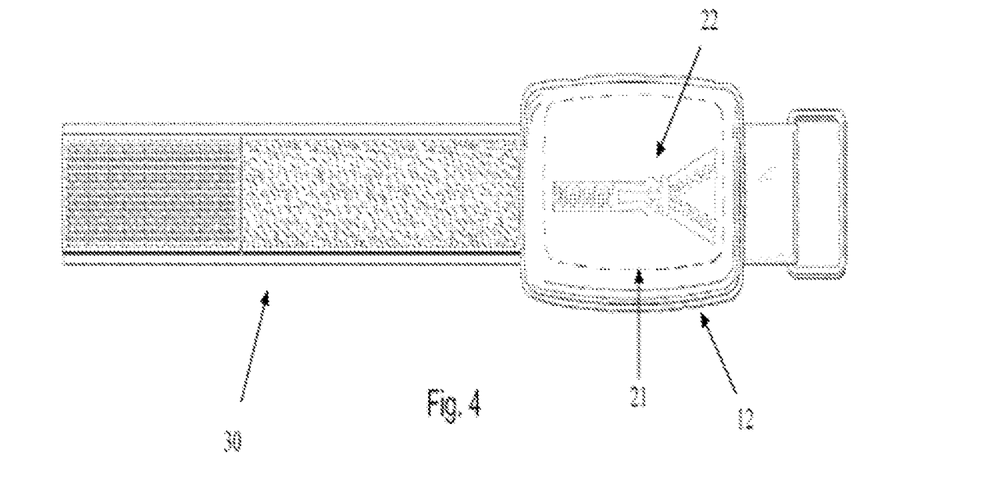
FIG. 4 is a top plan view of an alternative embodiment heat extracting device in accordance with the present invention.

In one embodiment, as shown in FIG. 2, the cold-maintaining substance 20 is contained within its own enclosure, or pack 21. The pack 21 may be sewn into the enclosure 12. Alternatively, the enclosure 12 may include a non-permeable inner lining that is able to contain the cold-maintaining substance 20 therein. This alternative embodiment would then forego the requirement of the pack 21. In the embodiment disclosed in FIGS. 1-3, it is contemplated that after the cooling properties wear off from the cold-maintaining substance 20 that the entire heat extracting device 10 is placed in a cooling environment (e.g., freezer). With reference to FIG. 4, in yet another embodiment 30, the content of the enclosure 12 is accessible to a user via an opening and closing mechanism 22, such as a zipper. Thus, the present invention may utilize both re-usable and one-time use disposable packs 21. A user may wish to replace the pack 21 with another newly-cooled pack after the cooling effects of the initial pack 21 have worn off due to a sufficient amount of heat having been absorbed. It is envisioned that replaceable packs may be stored in freezers or portable coolers having the necessary refrigeration (e.g., ice) that maintains a cold temperature to the replaceable packs. In any case, by providing an opening and closing mechanism that allows access to the cold-maintaining substance 20, the user is able to efficiently continue the heat extraction contemplated by the present invention. Other examples of opening and closing mechanisms 22 include, but are not limited to, interlocking tongue and groove arrangements, hook and loop fastener arrangements, clasps/buttons, overlapping flaps, etc. The opening and closing mechanism 22 may be defined within any surface of the enclosure 12, or along the edges thereof (e.g., along the seams).

In yet another embodiment, the enclosure 12 or any other component of the heat extracting device 10 may have a storage compartment or connectivity element associated therewith. For example, a portion of the strap 13a substantially corresponding to the other side of the enclosure 12 when the heat extracting device 10 is in a secured position, may include a pouch sized to store items, such as identification of the user or paper/coin currency, therein. Alternatively, the enclosure 12, itself may include such an added pouch or similar compartment.

In use, the heat extracting device 10 (or replaceable gel pack 21) is taken from a refrigerated or frozen area, such as a freezer, and is secured around the palm 19 of either hand 18. During use, an individual may use multiple gel packs 21 to maximize the heat extraction after the existing gel pack's heat extraction efficiency has been reduced. It is to be understood that this amount of time may vary based on various factors including the ambient temperature in which the heat extracting device 10 is used, physiology of the user, and extent of physical exertion by the user. The heat extracting device 10 may perform the intended purpose of the present invention when the temperature of the gel pack 21 is cooler than the ambient temperature. Although the enclosure 12 may be used in an open palm or closed palm, the efficiency of heat extraction via the present invention is increased when the palm is open, as normal blood flow is less disrupted.

A study has been conducted to evaluate the effects of the present invention. The study was a non-blinded Intervention vs. Control study that compared the results of both groups in order to quantify how much the heat extraction device 10 cools the body and affects the individual utilizing the heat extraction device 10. The participants for the study were recruited from a large organized running group in Austin, Tex. in the summer of 2010. A total of 23 individuals were included, with 12 participants being female and 11 being male. The average age was 40.65 (range 27 to 57 years old). The participants reported their race as follows: 18 White or Caucasian, 1 Black or African American, 2 Asian or Pacific Islander, and 2 Other. 2 classified themselves as Hispanic. The overall population exercised an average of 4.91 days a week (range 3 to 7 days a week) with an average of 64.78 minutes per exercise session (range 25 to 180 minutes). Fifteen participants reported their primary form of exercise (i.e., form of exercise they do the most), as running/jogging, 3 reported cycling, and 5 reported Other. The population ran an average of 3.61 days a week (range 2 to 6 days), running an average of 5.15 miles during a running session (range 2 to 10 miles). The participants responded running an average of 20.96 miles in a usual week (range 10 to 60 miles).

The participants of the Intervention group were randomized to wear the heat extraction device 10 during their warm-up, running, and cool-down, along with pre-cooling and post-cooling in order to complete questionnaires about the device 10. The group had a total of 12 participants; 7 of the group were female and 5 were male. The group had an average age of 41.17 years old (range 27 to 52 years old). Nine classified themselves as White or Caucasian, 1 as Black or African American, 1 as Asian or Pacific Islander, and 1 as Other. One classified themself as Hispanic. The Intervention group exercised an average of 4.5 days per week (range 3 to 7 days), with an average of 70 minutes per exercise session (range 30 to 180 minutes). The participants reported running an average of 3.5 days per week (range 3 to 5 days), with an average of 4.63 miles per running session (range 3 to 8 miles), and an average of 19.5 miles ran in a usual week (range 12 to 30 miles).

The participants of the Control group were randomized to exercise without the heat extraction device 10 in order to capture the population's normal reaction to the exercise. The group had a total of 11 participants; 5 were female and 6 were male. The group had an average age of 40.09 years old (range 27 to 57 years old). Nine of the group classified themselves as White/Caucasian, 2 as Asian or Pacific Islander, and 1 as other. One classified themself as Hispanic. The Control group exercised an average of 5.36 days per week (range 4 to 7 days), with an average of 59.09 minutes per exercise session (range 25 to 90 minutes). The participants reported running an average of 3.73 days per week (range 2 to 6 days), with an average of 5.73 miles per running session (range 2 to 10 miles), and an average of 22.55 miles ran in a usual week (range 12 to 60 miles).

The two groups did not show any statistical significant difference in any category.

| Category | P-value |
| --- | --- |
| Sex | .56 |
| Age | .76 |
| Days of Exercise per Week | .10 |
| Minutes per Exercise Session | .45 |
| Days of Running per Week | .57 |
| Miles per Running Session | .18 |
| Miles Run per Week | .50 |

The materials used for this study ranged from questionnaires to running equipment. Every participant was interviewed and ran in the same location in order to maintain consistency. The appointments were done one at a time. Participants ran on an indoor treadmill. Each participant's heart rate was monitored using a monitor that was strapped to the chest (POLAR T31-CODED CS100). The monitor was strapped to the chest and the heart rate was read by a separate component, not located on the participant. The temperature was read by a tympanic digital thermometer (CVS Pharmacy Brand). The questionnaires used are as follows: an eligibility form written by the study director to be specific to the study, a demographics questionnaire also asking about exercise habits and written by the study director, a perceived exertion questionnaire (BORG RPE Scale), perceived heat stress questionnaire (US Air Force), questionnaire after exercise determining the participant's feelings towards the exercise and difficulty written by the study director, a market research questionnaire written by the study director, and before and after questionnaires to assess the heat extraction device 10 experience for the Intervention group, written by the study director.

The study procedures included a one-time appointment that lasted about 2 hours. The participant would arrive and be met by the study director. The director brought the participant upstairs to a room where the participant would sit at a table with the director. The first questionnaire that was administered was the eligibility questionnaire. A participant was ineligible if they were under 18, had any injuries that would cause them harm while exercising, had never run 5K before, or were not comfortable on a treadmill. Every subject was found eligible. Informed consent was then obtained. At this point, the demographics questionnaire was administered, asking for demographics as well as exercising habits. The participant then put on the heart rate monitor. Once complete, the participant was randomized by opening the next envelope. If the participant was randomized to wear the heat extraction device 10, they were given the device 10 and asked a questionnaire about the comfort while wearing the device 10. Then all participants were taken to the gym. They were given a bottle of water and permitted to drink as much as they were comfortable with drinking. The participants were allowed to stretch or do whatever activities they would normally do before a run. Initial heart rate and temperature were then taken. The subject would warm-up at whatever pace was comfortable for them for 5 minutes. Heart rate and temperature were taken at this point. Also, the Borg scale and the perceived heat stress scale were asked for from each participant. The 5K (3.1 miles) run then began. The subject was told to run/jog/walk at the pace that was comfortable and they could speed up or slow down at any time. Heart rate, pace, and distance were recorded every 2 minutes. At 1.5 miles, the participant paused the treadmill and heart rate and temperature were taken along with the Borg scale and perceived heat stress scale. These measurements were repeated at the end of the run at the 3.1 mile (5K) mark. The participant then, at a speed comfortable for them, performed a 5 minute cool down. After the cool down, temperature, heart rate, Borg scale, and perceived heat stress were taken again. The participants could then stretch or do whatever they would normally do after a run.

After the exercise portion of the study, the participants were taken back to the office and follow-up questionnaires were administered. An after exercise questionnaire was asked to determine how they felt after their exercise experience. Also, a final measure of heart rate, temperature, Borg scale, and heat stress were taken. A market research questionnaire to determine how they felt about the heat extraction device 10 was also administered.

Randomization was done using the R program. The randomized numbers were put on cards and then placed into envelopes with corresponding numbers. The participants were assigned a number consecutively as they entered the study. The randomization was for 40 participants using R. Analysis of the results was done in Excel. The graphs were created using the pivot-table function. Averages and Student t-tests were used to obtain p-values.

The Borg scale is a self-reported measure of perceived exertion. The scale asks the participant to rate their perception of exertion. The feeling of exertion should reflect how heavy and strenuous the exercise feels to them, combining all sensations and feelings of physical stress, effort, and fatigue. The Borg scale measures from 6 ("No exertion at all") to 20 ("Maximal exertion"). The Borg scale (perceived exertion) did not show any difference between the Control and the Intervention groups. There was no trend or statistical significance in the difference found.

The Heat Stress scale is a self-reported measure of heat stress. The scale asks the participant to rate their perception of heat stress. The scale measures from 0 "(no heat stress at all")  to 11 ("maximal heat stress"). The Heat Stress scale did show a difference between the Control and the Intervention group. A trend of the intervention group reporting on average lower perceived heat stress while exercising was discovered. There was no statistical significance found.

Heart rate was measured using a monitor worn around the chest. The heart rate was taken as an initial resting heart rate before any activity began, after the warm-up, in the middle of the 5K run (1.5 miles), at the end of the 5K run, after the cool down period, and at the end of the study as a final resting heart rate. There was no difference in the average heart rates at any point in the study until the Final Resting Heart Rate. The average Final Resting Heart Rate of the Control group is 84.09 and the average for the Intervention group is 74.17. The p-value is 0.0298. This difference is statistically significant and shows that the heat extraction device 10 can help to return heart rate faster to normal in relation to when the heat extraction device is not used.

Temperature was taken using a tympanic thermometer. It was taken as an initial resting temperature before any activity began, after the warm-up, in the middle of the 5K run (1.5 miles), at the end of the 5K run, after the cool down period, and at the end of the study as a final resting temperature. The graph of average temperatures, taken at the various times throughout the appointment, shows a trend of cooler temperatures in the Intervention group. The graph shows a trend, but none of the preceding differences were statistically significant. Once the exercise was over and the final questionnaires were completed, the Intervention and Control groups showed a drastically different result. The Final Resting Temperature was an average of 97.73° in the Control group and 97.23° in the Intervention group. The difference is statistically significant, p-value 0.0479.

As evidenced in the above study, the phenomenon of cooling the core temperature by cooling the palm of the hand has been demonstrated by using the heat extraction device. Using clinical evaluators of heart rate and temperature, the study showed results of improved heart rate recovery time and cooler core temperatures through pre-cooling with the heat extraction device, wearing the device during exercise, and post-cooling with the device. The self-evaluating measure of perceived exertion (Borg Scale) did not show any statistically significant difference between the two groups, but the perceived heat stress evaluation was lower on average in individuals that wore the heat extraction device during exercise.

The Borg scale had the same tendency in each group. There was no trend or statistically significant difference found. The perceived exertion did not show any statistically significant difference between the Control and Intervention groups. The cause is presumed to be due to the population used in the study in that the population that participated exercised more than the average population. Therefore, the 5K run would not be enough to make the population feel a higher level of exertion.

The Heat Stress index did show a trend showing the Intervention group reporting lower heat stress than the Control group. The Intervention group showed a slower climb in heat stress and peaked at a lower number of heat stress, on average. This is important due to the comfort level felt while exercising. The group using the heat extraction device showed a trend towards increasing the athlete's comfort during the 5K run, the most strenuous part of the study. This is incredibly significant to evidencing the device's efficacy and providing a better exercise experience for the user.

Heart rate had no statistically significant difference between the two groups until the final measure. It appeared that the study population was more fit than the average population. Therefore, a 5K run was not enough to push the population's limits and thus raise their heart rate to a maximum level. No statistically significant difference is shown during the warm up, 5K, or cool down periods. However, a statistically significant difference is found at the final resting heart rate measure. The study shows that using the heat extraction device before, during, and after exercise can improve the after effects of exercise, which could decrease recovery time and lower the stress on the body. This illustrates the benefits of using the heat extraction device to enhance the body's natural cooling process. Heart rate will return to normal quicker with the use of the heat extraction device. This can help an athlete recover quicker and feel more comfortable post-exercise.

Temperature also showed a strong trend. The Intervention group showed a lower temperature throughout the entire exercise. Wearing the heat extraction device during pre-cooling, during exercise, and post-cooling after exercise was proven to lower core temperature on average across the board. As the running activity progressed, the Intervention group's temperatures, on average, increased slower and peaked at a lower temperature at the end of 5 kilometers. Both groups showed a decrease in temperatures during the cool down period. At the end of the exercise portion, a final temperature was taken and the Intervention and Control group showed drastically different results. The trend of a cooler core temperature in the Intervention group supports the functionality of the heat extraction device. To show this trend and to have a statistically significant different result at the final recovering temperature measure is evidence that the heat extraction device successfully cools the body's core temperature.

The self-reported heat stress has a trend showing that those who wore the heat extraction device reported feeling lighter heat stress than those that did not wear the device. The heart rate, on average, of the individuals that wore the heat extraction device was statistically significantly lower and closer to their initial resting heart rate when compared to those that did not wear the device. The heart rate recovery time was less in those that wore the device. Most considerably, the temperature measure showed a significant trend towards a lower temperature in those that wore the heat extraction device before, during, and after exercise. The temperature graph shows a considerable difference, and the final resting temperature reading is statistically significantly lower in the group wearing the heat extraction device when compared with the controls. All of these measures provide evidence that the heat extraction device provides the wearer with a more comfortable exercising experience, as well as clinical benefits. The aforementioned findings can be used in connection with the present invention to aid athletes of all sorts to keep their temperatures down longer, to operate at their peak for a longer period of time, and to recover quicker following exercise.

The present invention may be used in various environments and physical exertion contexts. For example, in situations where a user is engaged in an extended and time sensitive activity (e.g., marathon) where it is not possible to efficiently replace the gel pack 21 by opening and closing the enclosure 12, it is contemplated that the replaceable gel packs 21 include a fastening mechanism (e.g., Velcro®, snaps, etc.) that allow them to be directly removably attached to the strap. In other activities, there may be sensitivities to reducing bulk of the enclosure 12. For example, weight reduction is important in a Yoga class to minimize discomfort, whereas thickness reduction is important for cyclists who need to be able to properly grip the handlebar. The present invention provides for these requirements through simple modifications made to the general concept disclosed herein. The present invention may also provide ancillary benefits. For example, a modified heat extracting device 10 for use in cycling may be engineered to provide additional vibration/shock absorbing qualities via suitably added material. In some fields, the present invention needs to be modified to address considerations inherent to that field. For example, use of the present invention in the medical field may require that the heat extracting device 10 be hyper-allergenic or contain bactericidal agents. In a gardening context or any other activity involving use of the entire hand, the heat extracting device 10 may be designed to accommodate a free range of motion for the fingers.

Although the present invention has been described in connection with a palm 19, the principles of the present invention may be applied to other body parts with little to no modification made to the construction of the heat extracting device 10 outlined herein. For example, the heat extracting device 10 may be fitted over the knuckles or around the wrist. Furthermore, the present invention may be used with soles of feet for heat extraction/transfer during exercise or working in hot conditions. Conversely, the present invention may encompass hot or warm contact to palms of hands and soles of feet for heat insertion/transfer during exercise or working in cold conditions. In such application, for example, the enclosure 12 may be adapted to comfortably contour to an individual's sole. An alternative gel pack may be embodied as a shoe insert or may include a strap for securing the gel pack to an individual's foot.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A method for extracting heat from a human body using a device adapted removably to be attached to a hand of the human so as to contact a palm portion of the hand, wherein the device comprises:
   (i) an enclosure containing a cold-maintaining substance; and
   (ii) securing means attached to the enclosure for securing the enclosure against the palm portion, the securing means comprising a first strap extending from a first end of the enclosure, wherein the first strap includes on one side thereof a hook and loop fastener arrangement, and a buckle fluidly secured to a second end opposite the first end of the enclosure, wherein the buckle is sized to receive the first strap therethrough;
   the method comprising the steps of:
   (a) placing the device in a refrigerated or frozen location;
   (b) removing the device from the refrigerated or frozen location;
   (c) securing the device against the palm portion; and
   (d) engaging in a physical exertion activity,
   wherein the step of securing the device against the palm portion includes the steps of:
   (1) holding the enclosure against the palm portion;
   (2) looping a free end of the first strap around a back of the hand in a first direction;
   (3) inserting the free end of the first strap through the buckle and looping the free end across the back of the hand in a second direction opposite the first direction; and
   (4) securing a plurality of hooks of the hook and loop fastener arrangement to a plurality of loops of the hook and loop fastener arrangement.

2. The method of claim 1, wherein the cold-maintaining substance comprises a gel containing water and a sodium salt of cross-linked polyacrylic acid.

* * * * *